US009125693B2

(12) United States Patent
Sugawara et al.

(10) Patent No.: US 9,125,693 B2

(45) Date of Patent: Sep. 8, 2015

(54) SCREW GUIDE TEMPLATE, SCREW GUIDE TEMPLATE SYSTEM, DRILLING METHOD, AND SPINAL FIXATION METHOD

(75) Inventors: Taku Sugawara, Akita (JP); Kazuo Mizoi, Akita (JP); Naoki Higashiyama, Akita (JP); Hidenori Ono, Tokyo (JP); Hisayuki Sugiyama, Tokyo (JP)

(73) Assignees: AKITA UNIVERSITY, Akita-shi, Akita (JP); ONO & CO., LTD., Tokyo (JP)

(*) Notice: Subject to any disclaimer, the term of this patent is extended or adjusted under 35 U.S.C. 154(b) by 223 days.

(21) Appl. No.: 13/700,371

(22) PCT Filed: May 30, 2011

(86) PCT No.: PCT/JP2011/062405

§ 371 (c)(1), (2), (4) Date: Jan. 23, 2013

(87) PCT Pub. No.: WO2011/149106

PCT Pub. Date: Dec. 1, 2011

(65) Prior Publication Data

US 2013/0116700 A1 May 9, 2013

(30) Foreign Application Priority Data

May 28, 2010 (JP) ................................ 2010-123001

(51) Int. Cl.

*A61B 17/58* (2006.01)
*A61B 17/60* (2006.01)

(Continued)

(52) U.S. Cl.

CPC ......... *A61B 17/7076* (2013.01); *A61B 17/1757* (2013.01); *A61B 2017/00526* (2013.01); *A61B 2017/568* (2013.01); *A61B 2019/502* (2013.01)

(58) Field of Classification Search

CPC ........... A61B 17/7076; A61B 17/1757; A61B 2017/00526; A61B 2019/502; A61B 2017/568

USPC ...................... 606/86 A, 96–98, 104, 46, 914

See application file for complete search history.

(56) References Cited

U.S. PATENT DOCUMENTS 5,437,677 A * 8/1995 Shearer et al. .................. 606/96
2004/0073229 A1* 4/2004 Yang ............................ 606/104

(Continued)

FOREIGN PATENT DOCUMENTS

JP 6-48611 U 7/1994
JP 3927487 B2 3/2007

(Continued)

OTHER PUBLICATIONS

International Search Report mailed Jun. 28, 2011; PCT/JP2011/062405.

(Continued)

*Primary Examiner* — Christopher Beccia
*Assistant Examiner* — Diana S Jones
(74) *Attorney, Agent, or Firm* — Ladas & Parry LLP

(57) ABSTRACT

Provided are: a screw guide template, screw guide template system, and drilling method whereby a hole can be drilled in an accurate position of a member to be drilled, in an accurate direction; and a spinal fixation method whereby a spinal fixation screw can be inserted into an accurate position in an accurate direction. The screw guide template (20) comprises: a close-contact face (21) to be closely contacted to the member; and a through hole (22) having one opening (23*a*) on the close-contact face; the close-contact face has a shape in male-female relation with a surface shape (31) of the member including a portion (32) to be drilled; and when the close-contact face is closely contacted to the portion to be drilled, the opening and portion to be drilled overlap each other so that the through hole is coaxial with the hole to be drilled by the drilling means.

13 Claims, 12 Drawing Sheets

(51) Int. Cl.

| | |
|---|---|
| ***A61F 2/00*** | (2006.01) |
| ***A61B 17/70*** | (2006.01) |
| ***A61B 17/17*** | (2006.01) |
| *A61B 17/56* | (2006.01) |
| *A61B 17/00* | (2006.01) |
| *A61B 19/00* | (2006.01) |

(56) References Cited

U.S. PATENT DOCUMENTS

| | | | |
|---|---|---|---|
| 2004/0175686 | A1 | 9/2004 | Ono et al. |
| 2005/0234461 | A1 | 10/2005 | Burdulis, Jr. et al. |

FOREIGN PATENT DOCUMENTS

| | | | |
|---|---|---|---|
| JP | 2008-522665 | A | 7/2008 |
| JP | 2009-061132 | A | 3/2009 |
| JP | 4423362 | B2 | 12/2009 |
| JP | 2012-143379 | A | 8/2012 |
| WO | 2007/097854 | A2 | 8/2007 |
| WO | 2007097854 | A2 | 8/2007 |
| WO | 2008/138127 | A1 | 11/2008 |
| WO | 2008138137 | A1 | 11/2008 |

OTHER PUBLICATIONS

International Search Report; mailed Jun. 28, 2011; PCT/JP2011/062405.

* cited by examiner

SCREW GUIDE TEMPLATE, SCREW GUIDE TEMPLATE SYSTEM, DRILLING METHOD, AND SPINAL FIXATION METHOD

TECHNICAL FIELD

The present invention provides: a screw guide template; a screw guide template system including the screw guide template; and a drilling method and spinal fixation method using the screw guide template.

BACKGROUND ART

Spinal fixation surgery using an implant made of titanium has been widely performed for diseases causing instability of the spine such as spondylosis deformans and spine injuries. The spinal fixation is a surgical procedure in which to insert a titanium implant into the spine to fixate the position of the spine. Especially there occurs, during this kind of surgery, a problem of damaging the blood vessel or nerves by inserting a spinal fixation screw, which is one kind of implant, in an incorrect area of the spine.

In performing a surgical operation using a spinal fixation screw, a method is employed in which to preoperatively plan and check a place to insert the spinal fixation screw by using an X-ray radioscopy device. However, it is difficult by this method to plan an accurate direction of inserting the spinal fixation screw. Therefore, the probability of being able to insert the spinal fixation screw into the spine at an accurate position and in an accurate direction of insertion depends on surgeon's experience. In addition, a virtual navigation system has been used, which is based on an image taken by computed tomography before surgery. However, the problem is that a large error occurs. Patent Document 1 discloses a technique relating to a template for registration for use in a medical navigation system operation.

CITATION LIST

Patent Literature

Patent Document 1: Japanese Patent No. 4423362

SUMMARY OF THE INVENTION

Problems to be Solved by the Invention

It has been difficult, with conventional techniques, to drill a hole for inserting a fixation member such as a spinal fixation screw into an object, in an accurate portion to be drilled and in an accurate direction of drilling (the "portion to be drilled" refers to a part which becomes an opening of a hole to be drilled by a drilling means on a surface of a member to be drilled, which shall apply hereinafter; and the "direction of drilling" refers to a direction in which a hole to be drilled by a drilling means goes, which shall apply hereinafter). A lot of experiences are required to drill a hole for inserting the spinal fixation screw, into the spine in an accurate part to be drilled and in an accurate direction of drilling. The template described in Patent Document 1 is used only for simply putting a mark on a surface of the bone; and thus the above problems cannot be solved by the technique disclosed in Patent Document 1 either.

Accordingly, an object of the present invention is to provide a screw guide template by which a hole can be drilled in an accurate part of a member to be drilled and in an accurate direction of drilling. Another object of the present invention is to provide: a screw guide template system which enables drilling of a hole in an accurate part to be drilled and in an accurate direction of drilling, even in a narrow space where a it is difficult, with the screw guide template, to identify the part to be drilled; a drilling method by which a hole can be drilled in an accurate part of a member to be drilled and in an accurate direction of drilling; and a spinal fixation method by which a spinal fixation screw can be inserted into an accurate part of the spine to be inserted and in an accurate direction of insertion (the "part to be inserted" refers to a part into which a spine fixation screw is inserted, which shall apply hereinafter; and the "direction of insertion" refers to a direction in which to insert the spinal fixation screw, which shall apply hereinafter).

Means for Solving the Problems

The present invention will be described below. In order to make the present invention easy to understand, reference numerals given in the accompanying drawings are shown here in parentheses. However, the present invention is not limited to the embodiments shown in the drawings.

A first aspect of the present invention is a screw guide template (10, 20, 20' 50, 60) to determine a position and a direction of a hole (33) in drilling the hole into a member (30) by a drilling means, wherein the screw guide template comprises: a close-contact face (11, 21, 51, 61) to be brought into close contact with the member; and a through hole (12, 22, 52) having one opening (13, 23_a_, 53_a_) on the close-contact face; the close-contact face of the screw guide template has a shape which is in male-female relation with a shape of a surface (31) including a portion (32) of the member to be drilled; and when the close-contact face is closely contacted to the portion of the member to be drilled, the opening of the screw guide template and the portion of the member to be drilled overlap each other so that the through hole is coaxial with the hole to be drilled by the drilling means.

In the first aspect of the present invention and the present invention described below (hereinafter simply referred to as the "present invention"), the "drilling means" is not particularly limited as long as it can drill a hole into a member to be drilled. A drill can be one of the specific examples thereof. In addition, the "close contact" refers to a state that when a close-contact face of a template is superimposed on a surface of a member to be drilled (the "screw guide template" of the first aspect of the present invention and a "location template" to be described below are sometimes simply referred to as a "template"), a recess portion or a protrusion portion on one of the faces is fitted with a protrusion portion or a recess portion on the other face, thereby fixating the relative position thereof.

In the screw guide template (10, 20, 20', 50, 60) of the first aspect of the present invention, the close-contact face (11, 21, 51, 61) is preferably formed based on tomographic information of the member (30) to be drilled. Forming the close-contact face using the tomographic information of the member to be drilled easily enables the close-contact face to have a shape precisely corresponding to the surface shape of the member to be drilled.

The screw guide template (20', 50) of the first aspect of the present invention preferably comprises a hollow tube (40, 54) which communicates with the through hole (22, 52) and extends opposite to the close-contact face (21, 51); and the hollow tube preferably has a hollow portion which allows the drilling means to be inserted thereinto. With this configuration, the drilling means can be easily inserted into the through hole, as will be described below.

The screw guide template (20, 20', 60) of the first aspect of the present invention is preferably configured to comprise: a first member (20*a*) having one end portion (22*a*) of the through hole (22) and the close-contact face (21); and a second member (20*b*, 60*b*) having the other end portion (22*b*) of the through hole; an axis of the through hole is preferably determined by a relative position relation of the through hole of the first member and the through hole of the second member; and a position of the portion (32) to be drilled is preferably determined by the opening (23*a*) on the close-contact face of the first member. With this configuration, it is possible to easily define an inserting direction of the drilling means when it is inserted into the through hole, and therefore possible to easily drill a hole in an accurate part of the member to be drilled and in an accurate direction of drilling.

In the screw guide template (20, 20', 60) of the first aspect of the present invention, which comprises the first member (20*a*) and the second member (20*b*, 60*b*), the inner diameter of the through hole (22*b*) of the second member is preferably the same as the inner diameter of the through hole (22*a*) of the first member, or larger than the inner diameter of the through hole (22*a*) of the first member. With this configuration, the drilling means or a spinal fixation screw described below can be easily inserted.

In the screw guide template (20') of the first aspect of the present invention comprising the first member (20*a*), the second member (20*b*), and the hollow tube (40), one end portion of the hollow tube can be configured to communicate with the through hole (22*a*) of the first member, and the other end portion of the hollow tube can be configured to communicate with the through hole (22*b*) of the second member. With this configuration, it is possible to easily insert the drilling means from the through hole of the first member to the through hole of the second member.

In the screw guide template (20', 50) of the first aspect of the present invention comprising the hollow tube (40, 54), the hollow tube is preferably coaxial with the through hole (22, 52) and preferably has an inner diameter which is substantially the same as that of the through hole. With this configuration, it is possible to prevent instability and deviation of the position and the inserting direction of the drilling means inside the hollow tube, when it is inserted.

In the screw guide template (10, 20, 20', 50, 60) of the first aspect of the present invention, the length (x1, x2) of the through hole is preferably twice or more and more preferably three Limes or more as large as the outer diameter of the drilling means to be inserted into the through hole. In the present invention, the "length of the through hole" refers to a distance from an opening into which the drilling means is first inserted, to an opening which is superimposed on the portion to be drilled. As will be described later in detail below, in the configuration that the hollow tube is arranged in a manner to extend the through hole, the total of the lengths of the hollow tube and the through hole will be the "length of the through hole". With this configuration, it is possible to easily define an inserting direction of the drilling means when it is inserted into the through hole.

In the screw guide template (10, 20, 20', 50, 60) of the first aspect of the present invention, the length (x1, x2) of the through hole is preferably determined by a difference (z−y) between the length (y) of the hole to be drilled into the member (30) and the length (z) of the part of the drilling means which can be inserted into the through hole (12, 22, 52). With this configuration, it is possible to easily drill a hole of an intended length. Further, it is possible to drill a hole from the portion to be drilled without affecting a part which is farther (deeper) than the part intended to be drilled.

In the screw guide template (10, 20, 20', 50, 60) of the first aspect of the present invention, the inner diameter of the through hole (12, 22, 52, 62) is preferably 1.001 to 1.1 times and more preferably 1.001 to 1.05 times as large as the outer diameter of the drilling means to be inserted into the through hole. With this configuration, it is possible to prevent instability and deviation of the position and the inserting direction of the drilling means inside the through hole, when it is inserted.

The screw guide template (60) of the first aspect of the present invention is preferably provided with a plurality of close-contact faces (61*a*, 61*b*) arranged at a predetermined interval. With this configuration, the screw guide template can be easily fixated firmly onto the surface of the member to be drilled.

The screw guide template (10, 20, 20', 50, 60) of the first aspect of the present invention can be used in drilling, into spine (30), a hole in which to insert a spinal fixation screw to fixate the spine (30). Namely, the member to be drilled can be the spine, and the hole to be drilled into the spine can be a hole into which a spinal fixation screw is inserted. In the present invention, the "spinal fixation screw" is one kind of implant and refers to a screw used to fixate the spine.

A second aspect of the present invention is a screw guide template system to determine a position and a direction of a hole in drilling the hole into a member by a drilling means, wherein the screw guide template system comprises: the screw guide template (10, 20, 20', 50, 60) of the first aspect of the present invention; and a location template (5); the location template comprises: a close-contact face (1) to be brought into close contact with the member; and a through hole (2) having one opening (3) on the close-contact face; the close-contact face of the location template has a shape which is in male-female relation with a shape of a surface of the member including a portion to be drilled; and the through hole is formed such that the opening of the location template and the portion of the member to be drilled overlap each other when the close-contact face is closely contact to the portion of the member to be drilled.

A third aspect of the present invention is a drilling method by which to drill a hole into a member, the method comprising the steps of: forming in advance the close-contact face (11, 21, 51, 61) of the screw guide template (10, 20, 20', 50, 60) of the first aspect of the present invention such that it has a shape which is in male-female relation with a shape of a surface (31) including the portion (32) of the member (30) to be drilled; identifying the portion to be drilled by contacting the close-contact face to the surface of the member to thereby tightly fixate the screw guide template onto the surface including the portion of the member to be drilled; and drilling a hole into the portion of the member to be drilled by passing the drilling means into the through hole (12, 22, 52) of the screw guide template.

A fourth aspect of the present invention is a spinal fixation method by which to drill a hole into the spine and insert a spinal fixation screw into the hole, the method comprising the steps of: forming in advance the close-contact face (11, 21, 51, 61) of the screw guide template (10, 20, 20', 50, 60) of the first aspect of the present invention such that it has a shape which is in male-female relation with a shape of a surface (31) including a portion (32) of the spine (30) to be inserted; identifying the portion to be inserted by contacting the close-contact face to the surface of the spine to thereby tightly fixate the screw guide template onto the surface including the portion of the spine to be inserted; drilling a hole into the portion of the spine to be inserted by passing the drilling means into the through hole (12, 22, 52, 62) of the screw guide template; and inserting a spinal fixation screw into the hole formed by drilling.

Effects of the Invention

According to the screw guide template of the first aspect of the present invention, it is possible to drill a hole in an accurate part of a member to be drilled and in an accurate direction of drilling.

Additionally, according to the screw guide template system of the second aspect of the present invention, it is possible to drill a hole in an accurate part to be drilled and in an accurate direction of drilling, even in a narrow space where it is difficult, with the screw guide template, to identify the portion to be drilled.

Further, according to the drilling method of the third aspect of the present invention, it is possible to drill a hole in an accurate part of a member to be drilled and in an accurate direction of drilling.

Furthermore, according to the spinal fixation method of the fourth aspect of the present invention, it is possible to insert a spinal fixation screw into an accurate part of the spine to be inserted therewith and in an accurate direction of insertion.

MODE FOR CARRYING OUT THE INVENTION

Figure 1:
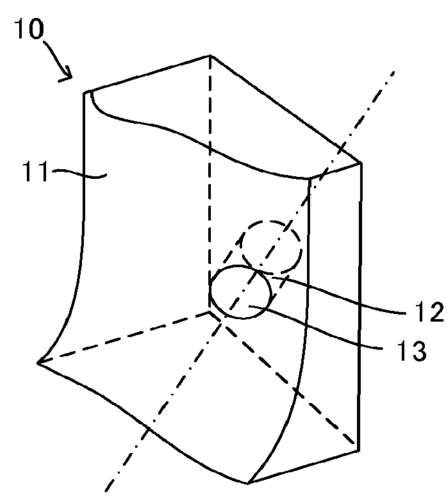
FIG. 1 is a perspective view schematically showing a screw guide template of the present invention according to a first embodiment.

The functions and benefits of the present invention described above will be apparent from the following modes for carrying out the invention. Hereinafter, the present invention will be described based on the embodiments shown in the drawings. However, the invention is not limited to these embodiments.

1. Screw Guide Template

1.1. First Embodiment

FIG. 1 is a perspective view schematically showing a screw guide template 10 of the present invention according to a first embodiment.

The screw guide template 10 determines a position and a direction of a hole in drilling the hole into a member to be drilled. The screw guide template 10 comprises: a close-contact face 11 to be closely contacted to a member to be drilled; and a through hole 12 having one opening 13 on the close-contact face 11. The close-contact face 11 has a shape which is male-female relation with a shape of a surface of the member including portion to be drilled. The screw guide template 10 is configured such that when the close-contact face 11 is brought into close contact with the surface of the member including the portion to be drilled, the opening 13 of the through hole 12 and the portion Lo be drilled overlap each other and an axis of the through hole 12 (a dashed line in FIG. 1) is coaxial with the hole to be drilled.

In using the screw guide template 10, the close-contact face 11 thereof is brought into close contact with the surface including the portion of the member to be drilled. A relative position of the screw guide template 10 and the member to be drilled is fixated by closely contacting the close-contact face 11 to the surface of the member to be drilled. In this state, a drilling means such as a drill is inserted into the through hole 12 to bore a hole into the member to be drilled. At this time, the opening 13 and the portion of the member to be drilled overlap each other as described above, so that the through hole 12 is coaxial with the direction in which to drill a hole. Therefore, it is possible to drill a hole in an accurate part to be drilled and in an accurate direction drilling.

In the screw guide template of the present invention, the inner diameter of the through hole is not particularly limited as long as it allows the drilling means to be inserted into the through hole. However, the inner diameter of the through hole is preferably 1.001 to 1.1 times and more preferably 1.001 to 1.05 times as large as the outer diameter of the drilling means to be inserted into the through hole. If the inner diameter of the through hole is too small, it is difficult to insert the drilling means into the through hole. If it is too large, the inserting position or inserting direction of the drilling means tends to be unstable and deviated inside the through hole at the time when it is inserted into the through hole.

Further, in the screw guide template of the present invention, the length of the through hole is not particularly limited. However, in order to prevent the inserting position and inserting direction of the drilling means from being unstable and deviated when inserting the drilling means into the through hole, it is preferable for the through hole to have some length. On the other hand, decreasing the thickness of the screw guide template in a range possible makes the screw guide template easy to use even in a narrow space. However, if the screw guide template is made too thin, it may not be able to have a through hole of enough length. If the through hole is too short, it is difficult to determine a direction of the hole (a direction in which to insert the drilling means) at the time of drilling the hole into the member by using the drilling means. From these viewpoints, it is preferable for the screw guide template of the present invention to have other configurations that are described below, rather than to be a plate-like body shown in FIG. 1 since it can have a through hole of certain length. For example, the length of the through hole is preferably twice or more and more preferably three times or more as large as the outer diameter of the drilling means. Further, it is preferable to determine the length of the through hole by a difference (z−y) between the length (y) of the hole to be drilled into the member and the length (z) of the part of the drilling means that can be inserted into the through hole. With this configuration, it is possible to drill a hole of an intended length easily and to drill a hole from the portion to be drilled without affecting a part farther (deeper) than the part intended to be drilled. For example, if the length of the through hole is larger than the difference between the length (y) of the hole to be drilled into the member and the length (z) of the part of the drilling means that can be inserted into the through hole, only a hole shorter than intended can be drilled with the screw guide template closely contacted to the member to be drilled. On the other hand, if the length of the through hole is smaller than the difference between the length (y) of the hole to be drilled into the member and the length (z) of the part of the drilling means that can be inserted into the through hole, the drilling means may go too deeply into the through hole, thereby drilling a hole longer than intended.

1.2. Second Embodiment

Figure 2:
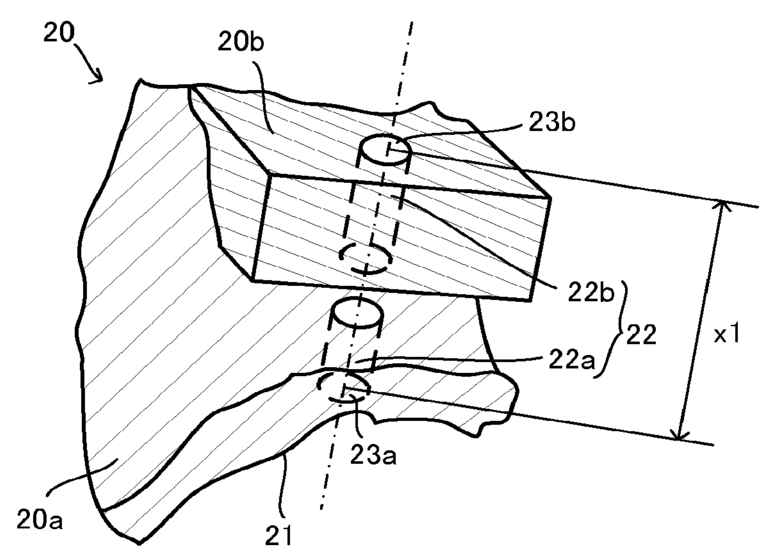
FIG. 2 is a perspective view schematically showing a screw guide template of the present invention according to a second embodiment.
Figure 3:
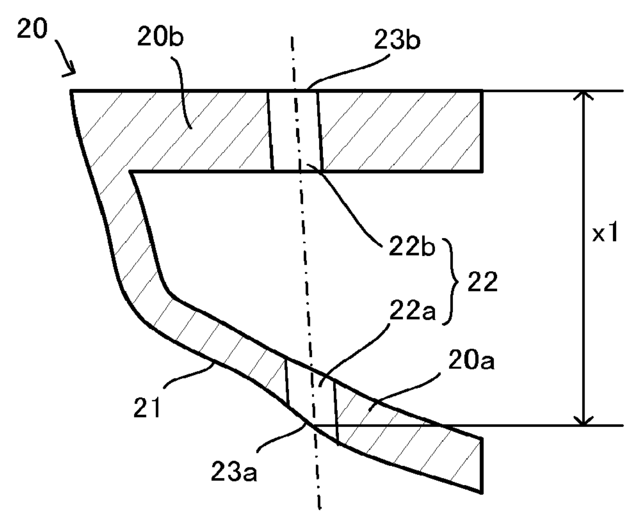
FIG. 3 is a schematic view of a cross section of the screw guide template shown in FIG. 2.

The screw guide template of the present invention is not particularly limited as long as it comprises such a close-contact face and a through hole as described above. Thus, it is not limited to the plate-like body shown in FIG. 1. FIG. 2 is a perspective view schematically showing a screw guide template 20 of the present invention according to a second embodiment. FIG. 3 is a schematic view of a cross section of the screw guide template 20 shown in FIG. 2, including a central axis (a dashed line in FIGS. 2 and 3) of a through hole 22.

The screw guide template 20 shown in FIGS. 2 and 3 is configured to comprise: a first member 20*a* having one end portion 22*a* of a through hole 22 (hereinafter sometimes referred to as a "through hole 22*a*") and a close-contact face 21; and a second member 20*b* having the other end portion 22*b* of the through hole 22 (hereinafter sometimes referred to as a "through hole 22*b*"). A central axis (a dashed line in FIGS. 2 and 3) of the through hole 22 is determined by a relative position relation of the through hole 22*a* of the first member 20*a* and the through hole 22*b* of the second member 20*b*. The through hole 22*a* and the through hole 22*b* are formed to be coaxial with each other. Namely, the through hole 22 has one central axis. In addition, a portion of a member to be drilled is determined by an opening 23*a* on the close-contact face 21 of the first member 20*a*.

As with the screw guide template 10, in using the screw guide template 20, the close-contact face 21 is brought into close contact with a surface including the portion of the member to be drilled. By closely contacting the close-contact face 21 to the surface of the member to be drilled, it is possible to fixate a relative position of the screw guide template 20 and the member to be drilled. In this state, a drilling means such as a drill is inserted into the through hole 22 to drill a hole into the member. At this time, the opening 23*a* and the portion of the member Le be drilled overlap each other as described above, so that the through hole 22 is coaxial with the direction in which to drill a hole. Therefore, it is possible to drill a hole into an accurate part to be drilled in an accurate direction of drilling.

As described above, in the screw guide template of the present invention, the inner diameter of the through hole is not particularly limited as long as it allows the drilling means to be inserted into the through hole. However, the inner diameter of the through hole is preferably 1.001 to 1.1 times and more preferably 1.001 to 1.05 times as large as the outer diameter of the drilling means to be inserted into the through hole. In a configuration that the through hole is separated into plural parts as in the screw guide template 20 shown in FIG. 2, the inner diameter of the through hole having an opening on the close-contact face is preferably in the above range, and the inner diameter of the other through hole is preferably the same as or larger than the inner diameter of the through hole having an opening on the close-contact face. That is, in the screw guide template 20, it is preferable for the inner diameter of the through hole 22*a* to be in the above range, and preferable for the inner diameter of the through hole 22*b* to be the same as or larger than the inner diameter of the through hole 22*a*. If the inner diameter of the through hole 22*b* is larger than that of the through hole 22*a*, the drilling means or a spinal fixation screw described below can be easily inserted into the through hole 22*a*.

In addition as mentioned above, in the screw guide template of the present invention, the length of the through hole is not particularly limited. However, it is preferably twice or more and more preferably three times or more as large as the outer diameter of the drilling means to be inserted into the through hole. Further, it is preferable to determine the length of the through hole by a difference (z−y) between the length (y) of the hole to be drilled into the member and the length (z) of the part of the drilling means that can be inserted into the through hole. In this case, the "length of the through hole" refers to a distance from the opening in which to first insert the drilling means, to the opening which is superimposed on the portion to be drilled. That is, when the through hole 22 is separated into plural parts as in the screw guide template 20, "x1" shown in FIGS. 2 and 3 (a distance from the center of the opening 23*b*, which is the opening in which to first insert the drilling means, to the center of the opening 23*a*, which is the opening to be superimposed on the portion to be drilled) is the length of the through hole 22.

1.3. Third Embodiment

Figure 4:
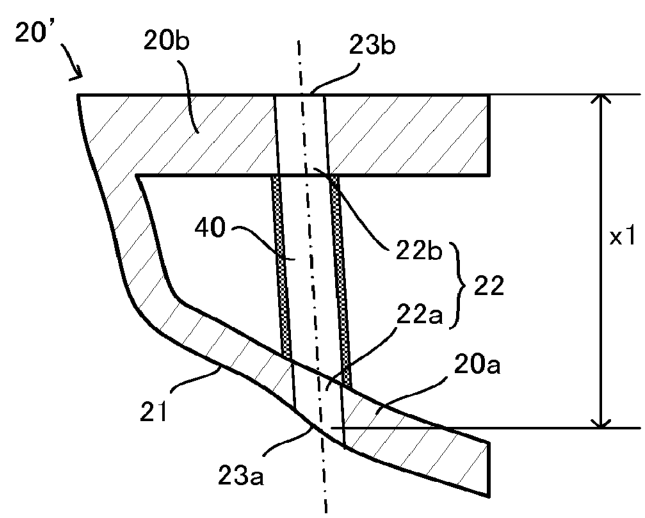
FIG. 4 is a cross-sectional view schematically showing a screw guide template of the present invention according to a third embodiment.

The screw guide template of the present invention will be described further with another embodiment. FIG. 4 is a schematic view of a cross section of a screw guide template 20' of the present invention according to a third embodiment, and corresponds to the cross-sectional view of FIG. 3. The screw guide template 20' is the same as the screw guide template 20 except that it comprises a hollow tube 40. Therefore, descriptions of the components other than the hollow tube 40 will be omitted.

The hollow tube 40 has one end communicating with a through hole 22*a* of a first member 20*a* and the other end communicating with a through hole 22*b* of a second member 20*b*; and has a hollow portion through which a drilling means used in drilling a hole into a member can be inserted. With the hollow tube 40 provided, it is possible to easily insert the drilling means from the through hole 22*b* to the through hole 22*a*.

The shape of the hollow tube 40 is not particularly limited as long as it allows the drilling means to be inserted from the through hole 22*b* into the through hole 22*a* when a close-contact face 21 of the screw guide template 20' is closely contacted to the member to be drilled. However, it is preferable for the hollow tube 40 to be cylindrical having an inner diameter which is substantially the same as that of the through hole 22, and to be coaxial with the through hole 22. The inner diameter of the hollow tube 40 is preferably 1.001 to 1.1 times and more preferably 1.001 to 1.05 times as large as the outer diameter of the drilling means. This is because it is possible to prevent the inserting position and inserting direction of the drilling means from being unstable and deviated inside the hollow tube 40 when it is inserted.

1.4. Fourth Embodiment

Figure 5:
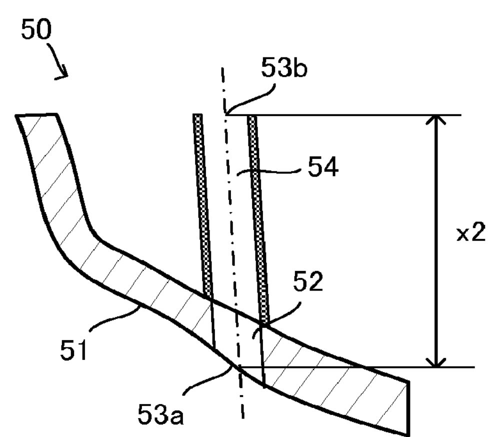
FIG. 5 is a cross-sectional view schematically showing a screw guide template of the present invention according to a fourth embodiment.

The screw guide template of the present invention will be described further with another embodiment. FIG. 5 is a schematic view of a cross section of a screw guide template 50 of the present invention according to a fourth embodiment, and corresponds to the cross-sectional views of FIGS. 3 and 4.

The screw guide template 50 shown in FIG. 5 comprises: a close-contact face 51; a through hole 52 having one opening 53 on the close-contact face 51; and a hollow tube 54. The close-contact face 51 can be the same as the close-contact faces 11, 21 of the screw guide templates 10, 20, 20', which have been described above. Therefore descriptions thereof will be omitted. The screw guide template 50 is configured such that when the close-contact face 51 is closely contacted to a face of a member to be drilled including a portion to be drilled, the opening 53 of the through hole 52 and the portion of the member to be drilled overlap each other, and an axis of the through hole 52 (a dashed line in FIG. 5) is coaxial with a hole to be drilled.

The hollow tube 54 has one end communicating with the through hole 52; extends opposite to the close-contact face 51; and has a hollow portion through which a drilling means used in drilling a hole into the member can be inserted. That is, the hollow tube 54 is arranged in a manner to extend the through hole 52. With the hollow tube 54 provided, it is possible to easily reduce the thickness of the screw guide template 50 (excluding the hollow tube 54) and secure the length of the through hole (including the hollow tube 54). The hollow tube 54 may be formed integrally with the through hole 52; or a hollow tube which is formed separately after the through hole 52 is formed may be provided as the hollow tube 54.

The shape of the hollow tube 54 is not particularly limited as long as it can guide the drilling means to the portion to be drilled when the close-contact face 51 is closely contacted to the face of the member including the portion to be drilled. However, it is preferable for the hollow tube 54 to be cylindrical having an inner diameter which is substantially the same as that of the through hole 52, and to be coaxial with the through hole 52. As described above, in the screw guide template of the present invention, the inner diameter of the through hole is not particularly limited as long as it allows the drilling means to be inserted into the through hole. However, it is preferably 1.001 to 1.1 times and more preferably 1.001 to 1.05 times as large as the outer diameter of the drilling means to be inserted into the through hole. That is, the inner diameter of the hollow tube 54 is also preferably 1.001 to 1.1 times and more preferably 1.001 to 1.05 times as large as the outer diameter of the drilling means. This is because it is possible to prevent the inserting position and inserting direction of the drilling means from being unstable and deviated inside the hollow tube 54 when it is inserted.

Additionally as described above, in the screw guide template of the present invention, the length of the through hole is not particularly limited. However, it is preferably twice or more and more preferably three times or more as large as the outer diameter of the drilling means. Further, it is preferable to determine the length of the through hole by a difference (z−y) between the length (y) of the hole to be drilled into the member and the length (z) of the part of the drilling means that can be inserted into the through hole. In the configuration of arranging the hollow tube in a manner to extend the through hollow, as shown in FIG. 5, the "length of the through hole" is the total of the length of the hollow tube and the length of the through hole. That is, in the screw guide template 50, "x2" shown in FIG. 5 (the total length of the hollow tube 54 and the through hole 52) is the length of the through hole.

1.5. Fifth Embodiment

Figure 6:
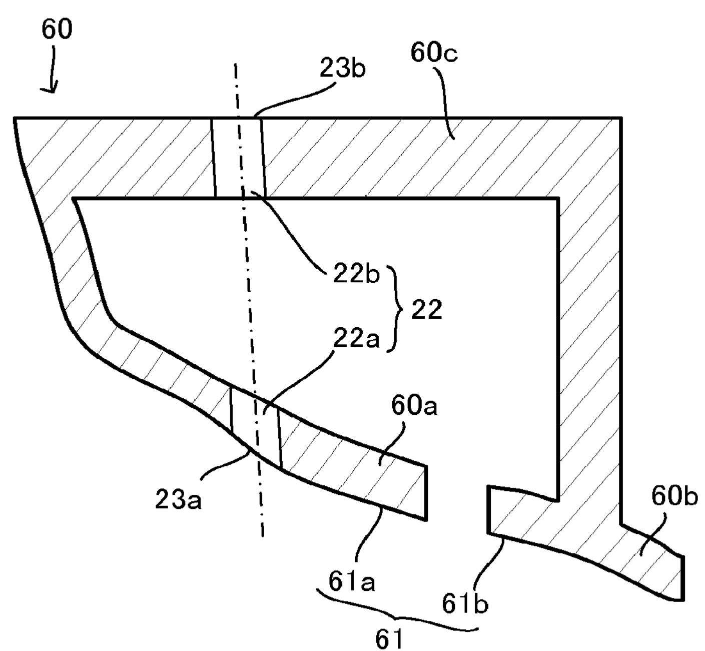
FIG. 6 is a cross-sectional view schematically showing a screw guide template of the present invention according to a fifth embodiment.

The screw guide template of the present invention will be described further with another embodiment. FIG. 6 is a schematic view of a cross section of a screw guide template 60 of the present invention according to a fifth embodiment, and corresponds to the cross-sectional views of FIGS. 3 to 5.

The screw guide template 60 shown in FIG. 6 comprises a close-contact face 61; and the close-contact face 61 comprises a first close-contact face 61*a* and a second close-contact face 61*b*. Further, the screw guide template 60 comprises: a first member 60*a* having one end portion 22*a* of a through hole 22 (through hole 22*a*) and the first close-contact face 61*a*; a second member 60*b* having the second close-contact face 61*b*; and a third member 60*c* having the other end portion 22*b* of the through hole 22 and connecting the first member 60*a* and the second member 60*b*.

With the configuration of arranging a plurality of close-contact faces of the screw guide template at a predetermined interval in this manner, the screw guide template can be fixated firmly onto the surface of the member to be drilled. FIG. 6 shows a configuration in which two close-contact faces are provided, but the screw guide template of the present invention is not limited to this configuration. That is, three or more close-contact faces may be arranged separately.

2. Screw Guide Template System

Next, the screw guide template system of the present invention will be described. The screw guide template system of the present invention comprises: the screw guide template of the present invention described above; and a location template.

As described above, the through hole of the screw guide template has certain length in order to fixate a position and direction of a drilling means to insert; and accordingly the screw guide template becomes thick to a certain extent. Therefore, in a narrow place where there is not much space above the member to be drilled, it is sometimes difficult to closely contact the screw guide template to the member to be drilled to identify the portion to be drilled. The screw guide template system of the present invention makes it possible to drill a hole in the narrow place where it is difficult to closely contact the screw guide template to identify the portion to be drilled, by first using the location template to put a mark on the portion to be drilled, and thereafter using the screw guide template to drill a hole as described above. Therefore, according to the screw guide template system of the present invention, a hole can be drilled in an accurate part to be drilled and in an accurate direction of drilling, even in a narrow area where it is difficult, with the screw guide template, to identify the portion to be drilled.

Figure 7:
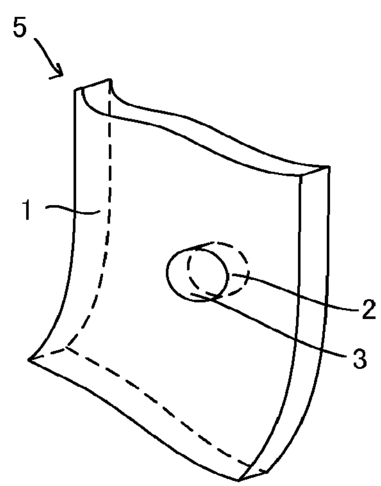
FIG. 7 is a perspective view schematically showing a location template according to one embodiment.

Hereinafter, the location template will be described with reference to FIG. 7. FIG. 7 is a perspective view schematically showing a location template 5 according to one embodiment.

The screw guide template determines not only a position of the hole but also a direction of the hole at a time when the hole is drilled into a member by a drilling means. On the other hand, the location template 5 is used to specify the position of the hole at the time of drilling the hole into the member. Therefore, the location template 5 does not need to be as thick as the screw guide template. In view of placing it in a narrow space, the location template 5 is preferably as thin as possible.

The location template 5 comprises: a close-contact face 1 to be closely contacted to a member to be drilled; and a through hole 2 having one opening 3 on the close-contact face 1. The close-contact face 1 has a shape which is male-female relation with a shape of a surface of the member including a portion to be drilled. The location template 5 is configured such that when the close-contact face 1 is closely contacted to the surface of the member including the portion to be drilled, the opening 3 of the through hole 2 and the portion to be drilled overlap each other.

In using the location template 5, the close-contact face 1 thereof is brought into close contact with the surface of the member including the portion to be drilled. A relative position of the location template 5 and the member to be drilled is fixated by closely contacting the close-contact face 1 to the surface of the member to be drilled. In this state, a marker is inserted into the through hole 2 to mark the member to be drilled. At this time, the opening 3 and the portion of the member to be drilled are superimposed on each other as described above, and therefore it is possible to put a mark on the accurate portion to be drilled.

In the location template, the inner diameter of the through hole is not particularly limited as long as it allows the marker to be inserted into the through hole. However, it is preferably 1.001 to 1.1 times and more preferably 1.001 to 1.05 times as large as the outer diameter of the marker to be inserted into the through hole. If the inner diameter of the through hole is too small, it is difficult to insert the marker into the through hole. If it is too large, the inserting position of the marker tends to be unstable and deviated in the through hole when it is inserted into the through hole. The marker to be used in the present invention is not particularly limited as long as it can mark the member to be drilled.

3. Member to be Drilled

A target object to be drilled using the screw guide template or the screw guide template system of the present invention is not particularly limited. For example, the member to be drilled can be spine; and the screw guide template or the screw guide template system of the present invention can be used when drilling, into the spine, a hole in which to insert a spinal fixation screw.

Figure 8:
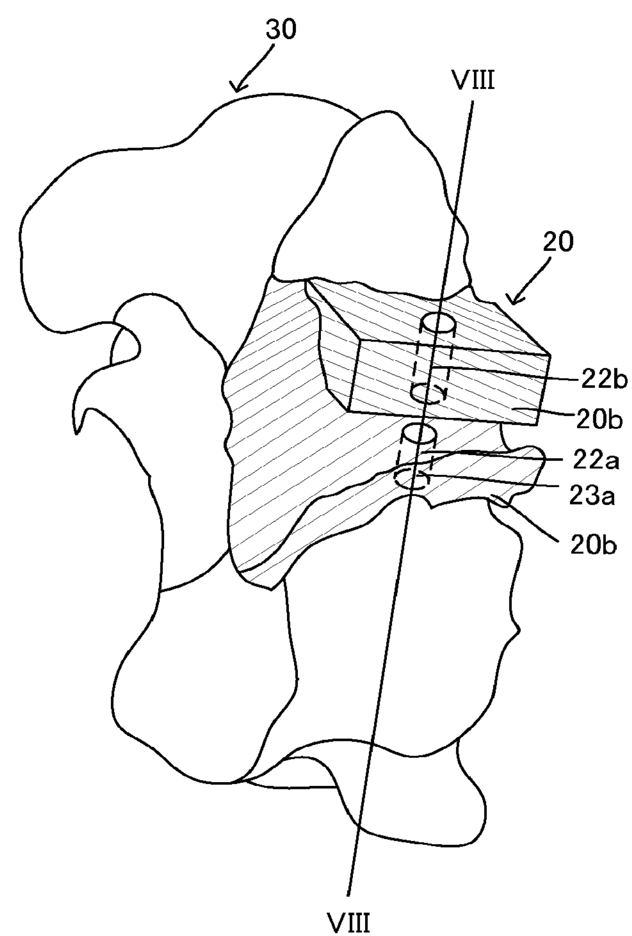
FIG. 8 is a perspective view schematically showing a manner in which the screw guide template shown in FIG. 2 is closely contacted to the spine.
Figure 9:
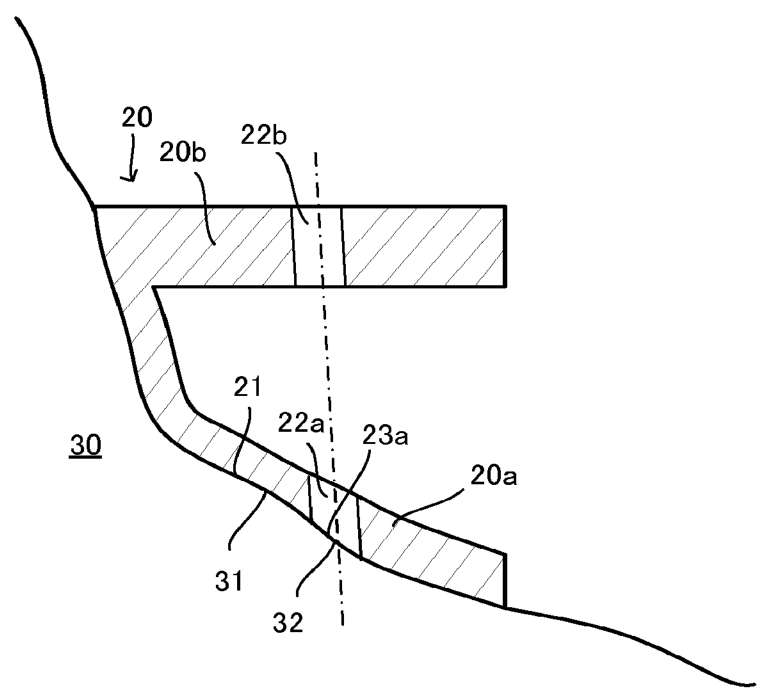
FIG. 9 is a schematic view partially showing a cross section taken along VIII-VIII shown in FIG. 8.
Figure 10:
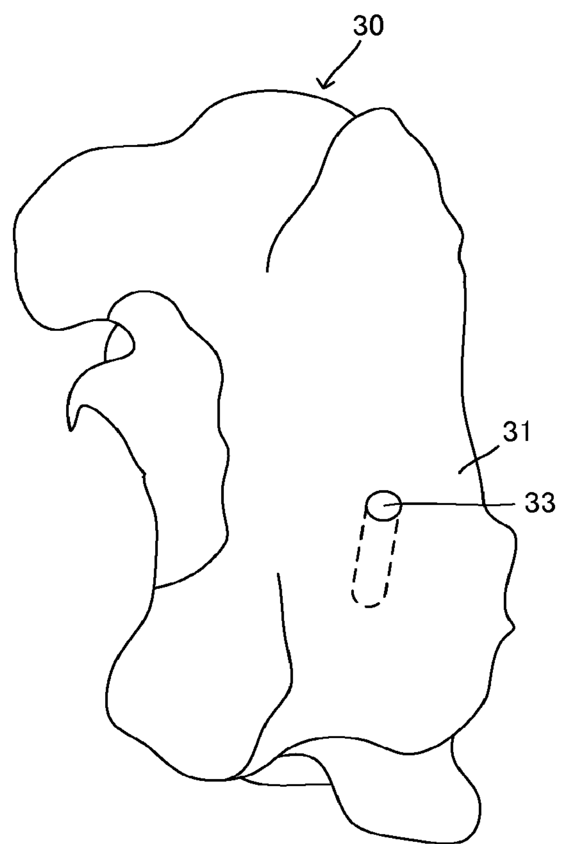
FIG. 10 is a perspective view schematically showing the spine having a hole drilled thereinto.

A method of using the screw guide template of the present invention will be described by giving as an example a case of drilling, into the spine being the member to be drilled, a hole in which to insert a spinal fixation screw, by using the screw guide template 20. FIG. 8 is a perspective view schematically showing a manner in which the screw guide template 20 is closely attached to the spine 30. FIG. 9 is a schematic view partially showing a cross section taken along VII-VII in FIG. 8. FIG. 10 is a perspective view schematically showing the spine 30 into which a hole 33 is drilled by using the screw guide template 20.

First, the close-contact face 21 of the screw guide template 20 is brought into close contact with a surface 31 of the spine 30 that includes a portion to be drilled (a portion to be inserted with a spinal fixation screw), as shown in FIGS. 8 and 9. At this time, the opening 23*a* of the screw guide template 20 and the portion 32 of the spine 30 to be drilled overlap each other, and thereby the through hole 22 becomes coaxial with the direction in which to drill a hole. In this state, a drilling means such as a drill is inserted into the through hole 22 to drill, into the spine 30, a hole 33 in which to insert the spinal fixation screw (see FIG. 10).

In this manner, the hole 33 in which to insert the spinal fixation screw can be drilled in accurate portion 32 to be inserted and in an accurate direction of insertion. Therefore, with the screw guide template of the present invention, it is possible to easily guide the spinal fixation screw to fixate the spine accurately to the portion to be inserted and insert it in an accurate direction of insertion, without necessitating an expensive device such as a navigation system.

Further, when the screw guide template of the present invention is used under the navigation system, the spinal fixation screw can be easily inserted more precisely than ever before.

In the case of using the screw guide template of the present invention in drilling, into the spine, a hole in which to insert the spinal fixation screw, the screw guide template of the present invention may be made for each portion of the spine to be given a surgical operation, as described below. As a result, it is possible to prevent the possibility of contacting the close-contact face of the template to an incorrect position of the spine. Therefore, with the screw guide template of the present invention in the above manner, it is possible to guide the spinal fixation screw with high precision.

4. Production Method of a Template

A production method of a template is not particularly limited, but it is preferable to form a close-contact face based on the tomographic information of a member to be drilled, for example. In drilling a hole using a template, the close-contact face thereof needs to have a shape which is in male-female relation with a surface shape of a member to be drilled. It is possible to reproduce the surface shape of the member to be drilled from the tomographic information, with high precision (error of not more than 0.1 mm). Therefore, with the tomographic information, the close-contact face in a shape that allows close and accurate contact with the surface of the member to be drilled can be easily formed. The production method of a template will be described with specific examples.

First, the tomographic information of the member to be drilled is obtained. The tomographic information can be obtained by perspective measurement or contour measurement, employing one of the known methods such as X-ray CT (X-ray Computer Tomography), MRI (Magnetic Resonance Imaging) and ultrasound imaging, or two or more thereof in combination.

Then, thus obtained tomographic information is turned into three-dimensional data to obtain three-dimensionally produced steric surface image data of the member to be drilled. For example, a widely available software “Mimics” can be used to turn the tomographic information obtained by X-ray CT or MRI into three-dimensional data. IL is possible to process and edit the three-dimensional image by reading the tomographic information using “Mimics”. With “Mimics”, it is possible to read the slice image of X-ray CT and MRI to extract the region of interest and create the three-dimensional surface image data. Further, it is possible to display on a display screen the three-dimensional image of the external contour and internal structure of the member to be drilled seen at an arbitrary angle. For the image processing, a standard format called “DICOM (Digital Imaging and Communication in Medicine) data” can be employed. “DICOM data” enables extraction of the region of interest, which is a portion intended to be made into three-dimensional data, from the above tomographic information by threshold and various segmentation functions of “Mimics”. Furthermore, the obtained tomographic information can be applied to selective laser sintering, optical fabrication and so on described below by being converted into two-dimensional DICOM data once and further converted into STL format data of surface type.

Next, a life-size model of the member to be drilled is formed by using the three-dimensionally produced steric surface image data of the member to be drilled. The model can be formed by such methods as stereolithography, ink-jet fabrication, powder binding, paper lamination, and selective laser sintering.

The above model is a life-sized model of the member to be drilled. Therefore with this model, it is possible to check a close-contact position, close-contact state, and close-contact precision of the template in drilling. As such, the model can be effectively used for examining the drilling procedure before drilling a hole, or for practicing drilling. In view of using this model for simulation of drilling and the like, it is preferable to make the model out of a material close to the actual member to be drilled. For example, when the member to be drilled is the spine, it is preferable to make a model by selective laser sintering using thermoplastic resin powder with inorganic material mixed therein (see Japanese Patent No. 3927487). The reason is that it enables three-dimensionally reproducing a life-sized model having a three-dimensional shape and hardness close to that of the spine, and an internal structure of the bone of the spine with precision and accuracy.

After the above model is formed, a surface in a predetermined position (a face including a portion to be drilled) of the model, as a press mold, is pressed to a mold (e.g. a plaster mold) of a predetermined size, thereby transferring the surface shape of the model thereto. The part where the surface shape of this model has been transferred can be a close-contact face of the template.

In this manner, a template having a close-contact face can be produced. In addition, the template also comprises a through hole in which to insert a drilling means. A method of forming the through hole is not particularly limited. It may be formed in a predetermined position and direction by using a drill or the like, after a template not comprising a through hole is made in the above manner. It is also possible to form the through hole in which to insert the drilling means separately. That is, it is possible to drill a hole into a template not comprising a through hole after making the template, and insert a hollow tube for forming a through hole into this hole, so that this hollow tube for forming the through hole can be the through hole in which to insert the drilling means. Further, in the case of arranging a hollow tube communicating with a through hole as in the above described third and fourth embodiments, the hollow tube may be attached after the through hole is provided to the template. It is also possible to arrange the hollow tube integrally with the above hollow tube for forming a through hole. The number of through holes to be provided to one template is not particularly limited, and an appropriate number of through holes may be formed depending on the number of holes to be drilled.

The material of the template is not particularly limited as long as it has appropriate hardness. However, if the member to be drilled is part of the living body such as the spine, the material of the template needs to be biocompatible. Examples of the bicompatible materials include: a synthetic resin, rubber, inorganic material, inorganic powder, and composite material thereof. When the member to be drilled is the spine, a sterilization treatment is given to the template. The sterilization method is not particularly limited, examples of which includes gas sterilization and coating.

Next, another specific example of the production method of a template will be described.

After making a model in the above manner, three-dimensional surface image data of a surface in a predetermined position (a face including a portion to be drilled) of the model is obtained by a non-contact laser scanning device. Then, a close-contact face of a template is formed based on the three-dimensional surface image data of the surface of the model. Thereby, a template having the close-contact face can be produced.

The method of producing a template based on the three-dimensional surface image data is not particularly limited, and various molding methods may be adopted. For example, such production methods as stereolithography, ink-jet fabrication, powder binding, paper lamination, and selective laser sintering can be suitable employed. When making a template by these methods, it is possible to arrange a through hole and a hollow tube in the above described manner after making a template having a close-contact face as above. It is also possible to carry out data processing of adding data of a through hole to three-dimensional surface image data of a template, thereby producing a template having a through hole from the data.

In the present invention, when making a template by selective laser sintering, a synthetic resin powder can be used as a material thereof. The synthetic resin powder is not particularly limited. For example, it is possible to use a powder of nylon, polycarbonate, polyester, polyacetal, polyethylene, polypropylene, polyvinyl chloride, polystyrene, polybutylene, ABS resin, cellulose-based resin, acrylic resin, epoxy resin, and fluorine resin. Among these, nylon can be used favorably. Further, nylon-12 can be used especially favorably.

In addition, when making a template by stereolithography, a light curing resin can be used as a material thereof. The light curing resin is not particularly limited. For example, it is possible to use a known light curing resin of acrylate type, epoxy type, or the like.

By using a material such as a transparent resin as a raw material in making the template of the present invention by selective laser sintering, stereolithography, or the like, it is possible to produce a transparent template. The transparent template is preferable from an operating viewpoint since a surface of the member to be drilled which is to be closely contacted with the template can be visually checked when contacting the template closely to the member.

Furthermore, a template can be produced by a below described method as well.

After obtaining three-dimensional surface image data of a member to be drilled in the above manner, data processing is performed in which to subtract the three-dimensional surface image data from a cuboid of a predetermined size. Through this processing, it is possible to form three-dimensional surface image data of a template having a close-contact face made out of the three-dimensional surface image data of the spine as a press mold.

Furthermore, the three-dimensional surface image data of the spine is duplicated and moved in certain amount (the amount equivalent to the thickness of a template to be produced) toward a face opposite to the close-contact face; and the duplicated data thus moved and the original three-dimensional surface image data are subtracted. Thereby, three-dimensional surface image data of a template can be formed which has a close-contact face made out of the three-dimensional surface image data of the spine as a press mold, and also has a face of substantially the same shape on the opposite side of the close-contact face.

Then, a template can be made based on these three-dimensional surface image data of the template by various molding methods as described above.

The production method of a template not using a model is effective in a case when it is unnecessary to use a life-sized model of a member to be drilled for preliminary examination or for other purposes, because a template can be directly made solely without creating a model. Further, such methods are favorable in that the production steps are simple. In addition, there is an advantage that in the case of forming a face having the same shape as that of a close-contact face on the opposite side of the close-contact face, it is possible, at a time of contacting the template to the member to be drilled, to easily judge the position at which it is brought into close contact with the surface of the member.

5. Drilling Method

Figure 11:
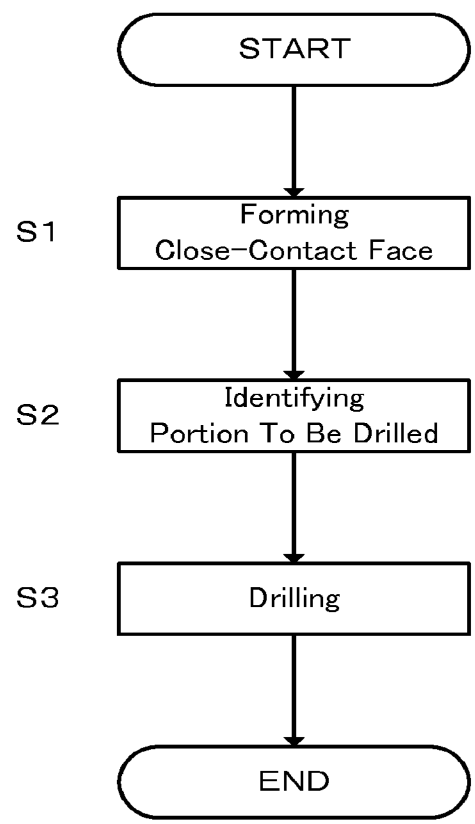
FIG. 11 is a flowchart schematically showing one example of a drilling method of the present invention.

Next, the drilling method of the present invention will be described with reference to a drawing. FIG. 11 is a flowchart schematically showing one example of the drilling method of the present invention.

As shown in FIG. 11, the drilling method of the present invention comprises: a close-contact face formation step S1; a drilling portion identification step S2; and a drilling step S3. These steps will be explained below.

The close-contact face formation step S1 is a step of forming a close-contact face of a screw guide template such that it has male-female relation with a shape of a surface of a member to be drilled which includes a portion to be drilled. The formation method of the close-contact face has already been explained in the descriptions of the production method of a template. Therefore descriptions thereof will be omitted.

In a case of using a location template, a close-contact face of the location template is formed in this step S1 as well such that it has male-female relation with a shape of a surface of a member to be drilled which includes a portion to be drilled.

The drilling portion identification step S2 is a step of identifying the portion to be drilled by contacting the close-contact face of the screw guide template to the surface of the member to be drilled to thereby tightly fixate the screw guide template onto the surface of the member including the portion to be drilled. As described above, the screw guide template is formed such that an opening of the screw guide template and the portion of the member to be drilled overlap each other at the time when the close-contact face of the screw guide template is brought into close contact with the portion of the member to be drilled. Therefore, it is possible to identify the portion to be drilled by contacting the close-contact face of the screw guide template to the surface of the member to be drilled to find the place where they are tightly fixated onto each other.

In the case of using the location template, the close-contact face of the location template is contacted to the surface of the member to be drilled in this step S2, to thereby tightly fixate the location template onto the surface of the member which includes the portion to be drilled and put a mark on the portion to be drilled. Thereafter, the close-contact face of the screw guide template is brought into contact with the surface of the member to be drilled, to thereby tightly fixate the close-contact face of the screw guide template and the surface of the member to be drilled onto each other.

The drilling step S3 is a step of drilling a hole into the portion of the member to be drilled by passing the drilling means into the through hole of the screw guide template, which is tightly fixated onto the surface of the member to be drilled in the above manner. As described above, the through hole of the screw guide template is formed to be coaxial with the direction in which to drill the hole. Therefore, a hole can be created in an accurate part to be drilled and in an accurate direction of drilling, by inserting the drilling means such as a drill into the through hole of the screw guide template and drilling a hole by the drilling means.

6. Spinal Fixation Method

Figure 12:
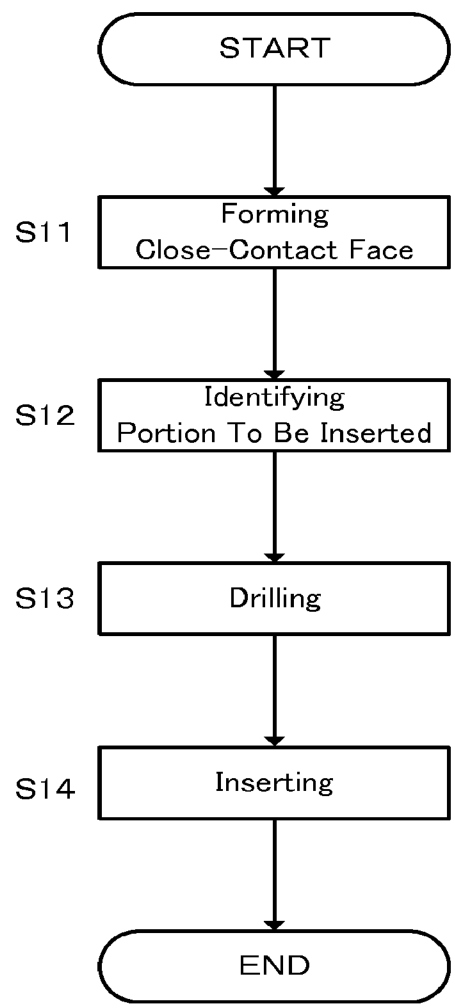
FIG. 12 is a flowchart schematically showing one example of a spinal fixation method of the present invention.

Next, the spinal fixation method of the present invention will be described with reference to a drawing. FIG. 12 is a flowchart schematically showing one example of the spinal fixation method of the present invention.

The spinal fixation method of the present invention is a method in which to drill a hole into the spine and insert a spinal fixation screw thereinto. As shown in FIG. 12, the spinal fixation method of the present invention comprises: a close-contact face formation step S11; an insertion portion identification step S12; a drilling step S13; and a insertion step S14. These steps will be explained below.

The close-contact face formation step S11 is a step of forming a close-contact face of a screw guide template such that it has male-female relation with a shape of a surface of the spine to be inserted which includes a portion to be inserted.

The insertion portion identification step S12 is a step of identifying the portion to be inserted by contacting the close-contact face of the screw guide template to the surface of the spine to thereby tightly fixate the screw guide template onto the surface of the spine including the portion Lobe inserted.

The drilling step S13 is a step of drilling a hole into the portion of the spine to be inserted by passing the drilling means into the through hole of the screw guide template.

Herein, the portion to be inserted is substantially the same as the portion to be drilled. Accordingly, except that the member to be drilled is the spine, the close-contact face formation step S11 is the same as the above close-contact face formation step S1; the insertion portion identification step S12 is the same as the above drilling portion identification step S2; and the drilling step S13 is the same as the above drilling step S3. Therefore, detailed descriptions of these steps will be omitted.

The insertion step S14 is a step of inserting a spinal fixation screw into the hole formed by drilling in the drilling step S13. As described above, the hole formed in the drilling step S13 (drilling step S3) is created in an accurate portion of the spine (member) to be drilled and in an accurate direction of drilling. Therefore, with the spine as the member Lo be drilled it is possible to insert the spinal fixation screw into an accurate part of the spine to be inserted therewith and in an accurate direction of insertion by inserting the spinal fixation screw into the hole formed in the drilling step S13.

The invention has been described above as to the embodiment which is supposed to be practical as well as preferable at present. However, it should be understood that the invention is not limited to the embodiment disclosed in the specification and can be appropriately modified within the range that does not depart from the gist or spirit of the invention, which can be read from the appended claims and the overall specification, and that a screw guide template, a screw guide template system, a drilling method, and a spinal fixation method with such modifications are also encompassed within the technical range of the invention.

DESCRIPTION OF THE NUMERALS

1 close-contact face
2 through hole
3 opening
5 location template
10 screw guide template

11 close-contact face
12 through hole
13 opening
20 screw guide template
20' screw guide template
20*a* first member
20*b* second member
21 close-contact face
22 through hole
22*a*, 22*b* through hole (end portion of through hole 22)
23*a* opening
30 spine
31 surface of the spine
32 portion to be drilled
40 hollow tube
50 screw guide template
51 close-contact face
52 through hole
53 opening
54 hollow tube
60 screw guide template
60*a* first member
60*b* second member
60*c* third member
61 close-contact face
61*a* first close-contact face
62*b* second close-contact face

The invention claimed is:

1. A screw guide template to be used in drilling, into member, a hole in which a spinal fixation screw to fixate the member is inserted, wherein the screw guide template comprises:

a close-contact face to be brought into close contact with the member; a through hole having one opening on the close-contact face;

a second close-contact face to be brought into close contact with the member;

a first member having one end portion of said through hole and said first close-contact face;

a second member having the other end portion of said through hole; and a hollow tube having a hollow portion which allows a drilling means to be inserted thereinto, further wherein:

the close-contact face of the screw guide template has at least one of male or female shape relative to a surface of the member including a portion to be drilled;

when the close-contact face is closely contacted to the portion of the member to be drilled, the opening of said screw guide template and the portion of the member to be drilled overlap each other so that said through hole is coaxial with the hole to be drilled by a drilling means;

a predetermined interval is provided between the first close-contact face and the second close-contact face;

an axis of the through hole is determined by a relative position relation of the through hole of said first member and the through hole of said second member;

a position of said portion to be drilled is determined by said opening on said first close-contact face of said first member;

an inner diameter of the through hole of said second member is the same as an inner diameter through hole of said first member, or larger than the inner diameter of the through hole of said first member; and one end portion of the hollow tube communicates with the through hole of said first member, and the other end portion of the hollow tube communicates with the through hole of said second member.

2. The screw guide template according to claim 1, wherein said close-contact face is made based on tomographic information of the member.

3. The screw guide template according to claim 1, comprising a hollow tube which communicates with said through hole and extends opposite to said close-contact face, wherein said hollow tube has a hollow portion which allows said drilling means to be inserted thereinto.

4. The screw guide template according to claim 3, wherein said hollow tube is coaxial with said through hole and an inner diameter of said hollow tube is 1.001 to 1.1 times as large as an outer diameter of said drilling means.

5. The screw guide template according to claim 1, wherein a length of said through hole is twice or more as large as an outer diameter of said drilling means.

6. The screw guide template according to claim 5, wherein a length of said through hole is three times or more as large as an outer diameter of said drilling means.

7. The screw guide template according to claim 1, wherein the screw guide template is made such that a length of said through hole corresponds to a difference (z−y) between a length (y) of the hole to be drilled into the member and a length (z) of a part of said drilling means which can be inserted into said through hole.

8. The screw guide template according to claim 1, wherein an inner diameter of said through hole is 1.001 to 1.1 times as large as an outer diameter of said drilling means.

9. The screw guide template according to claim 8, wherein an inner diameter of said through hole is 1.001 to 1.05 times as large as an outer diameter of said drilling means.

10. A screw guide template system to determine a position and a direction of a hole in drilling the hole into member by a drilling means, wherein the screw guide template system comprises; the screw guide template according to claim 1; and a location template;

said location template comprises: a close-contact face to be brought into close contact with the member; and a through hole having one opening on the close-contact face;

the close-contact face of said location template has a shape which is in male-female relation with a shape of a surface of the member including a portion to be drilled; and said through hole is formed such that the opening of said location template and the portion of the member to be drilled overlap each other when the close-contact face is closely contacted to the portion of the member to be drilled.

11. A drilling method by which to drill a hole into member, the method comprising the steps of:

forming in advance the close-contact face of the screw guide template according to claim 1 such that it has a shape which is in male-ferrule relation with a shape of a surface of the member including a portion to be drilled:

identifying said portion to be drilled by contacting the close-contact face to the surface of the member to thereby tightly fixate said screw guide template onto the surface of the member including the portion to be drilled; and drilling a hole into the portion of the member to be drilled by passing a drilling means into the through hole of said screw guide template.

12. A spinal fixation method by which to drill a hole into member and insert a spinal fixation screw into the hole, the method comprising the steps of:

forming in advance the close-contact face of the screw guide template according to claim 1 such that it has a shape which is in male-female relation with a shape of a surface of said member including a portion to be inserted;

identifying said portion to be inserted by contacting the close-contact face to the surface of said member to thereby tightly fixate said screw guide template onto the surface of said member including the portion to be inserted;

drilling a hole into the portion of said member to be inserted by passing a drilling means into the through hole of said screw guide template; and inserting a spinal fixation screw into the hole formed by drilling.

13. The screw guide template according to claim 1, wherein said hollow tube is coaxial with said through hole and an inner diameter of said hollow tube is 1.001 to 1.1 times as large as an outer diameter of said drilling means.

* * * * *